(12) United States Patent
Boynton et al.

(10) Patent No.: US 7,811,269 B2
(45) Date of Patent: *Oct. 12, 2010

(54) NEGATIVE PRESSURE ASSISTED TISSUE TREATMENT SYSTEM

(75) Inventors: Thomas A. Boynton, Floresville, TX (US); Teryl Blane Sanders, San Antonio, TX (US); Keith Patrick Heaton, Poole (GB); Kenneth William Hunt, Wimborne (GB); Mark Stephen James Beard, Wimborne (GB); David M. Tumey, San Antonio, TX (US); Lawrence Tab Randolph, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/364,264

(22) Filed: Feb. 28, 2006

(65) Prior Publication Data

US 2006/0149170 A1 Jul. 6, 2006

Related U.S. Application Data

(63) Continuation of application No. 09/939,166, filed on Aug. 24, 2001, now Pat. No. 7,004,915.

(51) Int. Cl.
*A61M 27/00* (2006.01)
(52) U.S. Cl. .................. 604/313; 604/315; 604/543
(58) Field of Classification Search .............. 601/6, 601/7, 9, 10, 11, 12; 604/313–315, 543; 602/41–43
See application file for complete search history.

(56) References Cited

U.S. PATENT DOCUMENTS 1,355,846 A  10/1920 Rannells (Continued)

FOREIGN PATENT DOCUMENTS

AU  87770/82  8/1982

(Continued)

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(Continued)

*Primary Examiner*—Danton DeMille

(57) ABSTRACT

A system for stimulating the healing of tissue comprises a porous pad positioned within a wound cavity, and an airtight dressing secured over the pad, so as to provide an airtight seal to the wound cavity. A proximal end of a conduit is connectable to the dressing. A distal end of the conduit is connectable to a negative pressure source, which may be an electric pump housed within a portable housing, or wall suction. A canister is positioned along the conduit to retain exudates suctioned from the wound site during the application of negative pressure. A first hydrophobic filter is positioned at an opening of the canister to detect a canister full condition. A second hydrophobic filter is positioned between the first filter and the negative pressure source to prevent contamination of the non-disposable portion of the system by exudates being drawn from the wound. An odor filter is positioned between the between the first and second hydrophobic filters to aid in the reduction of malodorous vapors. A securing means is supplied to allow the portable housing to be secured to a stationary object, such as a bed rail or intravenous fluid support pole. A means for automated oscillation of pressure over time is provided to further enhance and stimulate the healing of an open wound. A means for varying pump drive frequency and a means for managing a portable power supply are provided to increase battery life and improve patient mobility.

30 Claims, 4 Drawing Sheets

U.S. PATENT DOCUMENTS

| | | | |
|---|---|---|---|
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,003,373 A | 1/1977 | Spelio | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,468,219 A | 8/1984 | George et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,002,539 A * | 3/1991 | Coble et al. | 604/253 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,466,229 A * | 11/1995 | Elson et al. | 604/317 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,637,093 A | 6/1997 | Hyman et al. | |
| 5,645,081 A | 7/1997 | Argenta et al. | |
| 5,701,917 A * | 12/1997 | Khouri | 128/897 |
| 6,071,267 A | 6/2000 | Zamierowski | |
| 6,093,230 A | 7/2000 | Johnson, III et al. | |
| 6,135,116 A | 10/2000 | Vogel et al. | |
| 6,142,982 A | 11/2000 | Hunt et al. | |
| 6,235,039 B1 | 5/2001 | Parkin et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,348,777 B1 * | 2/2002 | Brown et al. | 320/160 |
| 6,398,767 B1 | 6/2002 | Fleischmann | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,004,915 B2 | 2/2006 | Boynton et al. | |
| 7,108,683 B2 * | 9/2006 | Zamierowski | 604/304 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0014022 A1 * | 1/2003 | Lockwood et al. | 604/315 |

FOREIGN PATENT DOCUMENTS

| | | |
|---|---|---|
| AU | 550575 A1 | 8/1982 |
| AU | 745271 | 4/1999 |
| AU | 755496 | 4/2003 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0 777 504 * | 10/1998 |
| EP | 0777504 | 10/1998 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 | 3/1991 |
| GB | 2 307 180 A | 5/1997 |
| GB | 2 329 127 B | 8/1999 |
| GB | 2 333 965 A | 8/1999 |
| JP | H01-120646 | 5/1989 |
| JP | H03-277369 | 12/1991 |

| | | |
|---|---|---|
| JP | 4129536 | 4/1992 |
| JP | 2000-176009 | 6/2000 |
| SG | 71559 | 4/2002 |
| WO | WO 80/02182 * | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 * | 2/1996 |
| WO | WO 97/18007 * | 5/1997 |
| WO | WO 99/13793 | 3/1999 |
| WO | WO 00/07653 | 2/2000 |
| WO | WO 00/21586 | 4/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 A1 | 5/2001 |
| WO | WO 01/37922 A2 | 5/2001 |
| WO | WO 03/018098 A2 | 3/2003 |

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al; "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 and Apr. 29, 1997.

PCT Written Opinion, PCT International Application PCT/GB96/02802; Sep. 3, 1997.

International Search Report for PCT International Application PCT/GB95/01983; Nov. 23, 1995.

PCT International Preliminary Examination Report for PCT International Application PCT/US02/27070; Jul. 6, 2004.

PCT Written Opinion for PCT International Application PCT/US02/27070; Feb. 5, 2004.

PCT International Search Report for International Application PCT/US02/27070; Jul. 3, 2003.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

PCT Invitation to Pay Additional Fees, International Application No. PCT/US02/27070, Dec. 5, 2002.

Orringer, Jay, et al; "Management of Wounds in Patients with Complex Enterocutaneous Fistulas"; Surgery, Gynecology & Obstetrics, Jul. 1987, vol. 165, pp. 79-80.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksa U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow U.S.S.R. 1967) (certified translation).

M. Schein, R. Saadia, J.R. Jamieson, and G.A.G. Decker, "The 'Sandwich Technique' in the Management of the Open Abdomen," British Journal of Sugery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

Japanese Official Action date mailed Sep. 16, 2008; Japanese Application No. 2003-522611.

Chinese Official Action date mailed Dec. 8, 2008; Chinese Application No. 200610165996.7.

European Official Action date mailed May 2, 2007; European Application No. 02766098.4.

Canadian Official Action date mailed Dec. 21, 2007; Canadian Application No. 2,458,285.

Korean Official Action date mailed Sep. 30, 2008; Korean Application No. 2008-7013734.

Restriction Requirement date mailed Sep. 3, 2003 for U.S. Appl. No. 09/939,166.

Non-Final Office Action date mailed Apr. 15, 2005 for U.S. Appl. No. 09/939,166.

Response filed Sep. 15, 2004 to Non-Final Office Action date mailed Apr. 15, 2005 for U.S. Appl. No. 09/939,166.

Final Office Action date mailed Dec. 13, 2004 for U.S. Appl. No. 09/939,166.

Response filed Feb. 14, 2005 to Final Office Action date mailed Dec. 13, 2004 for U.S. Appl. No. 09/939,166.

Notice of Allowance date mailed Mar. 15, 2005 for U.S. Appl. No. 09/939,166.

Notice of Allowance date mailed Sep. 27, 2005 for U.S. Appl. No. 09/939,166.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

European Search Report dated Apr. 1, 2009; European Patent Application No. 09152614.5-2320.

* cited by examiner

NEGATIVE PRESSURE ASSISTED TISSUE TREATMENT SYSTEM

CROSS-REFERENCE TO RELATED APPLICATION

This is a continuing application of application Ser. No. 09/939,166, filed on Aug. 24, 2001 now U.S. Pat. No. 7,004,915; this application also claims the priority of copending international application No. PCT/US2002/027070, filed Aug. 23, 2002, which designated the United States; the prior applications are herewith incorporated by reference in their entirety.

FIELD OF THE INVENTION

This invention relates generally to tissue treatment systems. More particularly this invention relates to vacuum assisted treatment systems that aid in the healing of open wounds.

BACKGROUND OF THE INVENTION

Vacuum induced healing of open wounds has recently been popularized by Kinetic Concepts, Inc. of San Antonio, Tex., by its commercially available V.A.C.® product line. The vacuum induced healing process has been described in commonly assigned U.S. Pat. No. 4,969,880 issued on Nov. 13, 1990 to Zamierowski, as well as its continuations and continuations in part, U.S. Pat. No. 5,100,396, issued on Mar. 31, 1992, U.S. Pat. No. 5,261,893, issued Nov. 16, 1993, and U.S. Pat. No. 5,527,293, issued Jun. 18, 1996, the disclosures of which are incorporated herein by this reference. Further improvements and modifications of the vacuum induced healing process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997 respectively, the disclosures of which are incorporated by reference as though fully set forth herein. Additional improvements have also been described in U.S. Pat. No. 6,142,982, issued on May 13, 1998 to Hunt, et al.

In practice, the application to a wound of negative gauge pressure, commercialized by Assignee or its parent under the designation "Vacuum Assisted Closure" (or "V.A.C.®") therapy, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return. As a result, V.A.C.® therapy has been highly successful in the promotion of wound closure, healing many wounds previously thought largely untreatable.

The frequency at which negative pressure is applied to the wound, as well as the frequency of the pressure change over time, has a direct impact on the rate of wound healing. A variation of pressure change over time, not provided by current vacuum assisted therapy devices, is thought to significantly increase the rate of wound healing. Similarly, a rapid return to normal activities for the patient receiving wound therapy, may also improve the rate of wound healing, as increased physical activity is often accompanied by increased vascular circulation, which in turn leads to improved blood flow at the wound site. One barrier to a return to normal activities is limited battery life, which is a result of the electrical power required to power existing vacuum assisted wound therapy systems. Additionally, frequent inspection of the wound site is required in order to ensure the wound is not becoming infected. However, a rapid return to normal activities must not preclude the precautions that must be utilized during use of vacuum assisted therapy to prevent inadvertent spillage of wound exudates from the canister, or entry of wound exudates into the pumping mechanism.

Additional limitations are associated with the use of fixed frequency oscillating pumps in the prior art. Such limitations are the result of the size of the pump required to maintain the desired negative pressure at the wound site, and/or a reduction in battery life due to the power required to operate the oscillating pumps. Oscillating pumps, as known in the art, are typically designed for limited operating conditions. For example, to maximize low pressure flow rate at a fixed frequency. Typically the mass and/or stiffness of various components are altered to change the resonant frequency of the pump under the design operating conditions. If the pressure across the pump increases, the stiffness of the system is increased by back pressure across the diaphragm of the oscillating pump. The resonant frequency of the pump changes and the fixed frequency drive is not driving the pump at the optimum frequency. As a result, flow rate drops quickly and the capability of the pump to drive air at high pressure is limited. Accordingly, in order to provide increased flow rate at higher pressures requires either a sacrifice in flow rate at low pressures, or a pump of significantly greater size, when utilizing a fixed frequency oscillating pump.

For the foregoing reasons, there is a need for a vacuum assisted wound treatment system that is capable of automated pressure change over time. Additionally, there is a need for a more efficient vacuum assisted wound treatment system, that allows the patient more mobility, while reducing the risk of exudate spillage or pump contamination.

It is therefore an object of the present invention to provide a vacuum assisted wound treatment system that provides a means for increasing the stimulation of cellular growth by a variation of pressure over time.

A further object is to provide a system that is capable of extended operation in the absence of an alternating current power supply.

An additional object of the present invention is to provide a sanitary and cost effective means for sampling fluids drawn from the wound site without necessitating removal of the canister, or disturbing of the wound site.

Still another object of the present invention is to provide a vacuum assisted wound therapy device that can be secured to an object so as to reduce the likelihood of disturbance to the device, while still allowing convenient placement for its operation.

SUMMARY OF THE INVENTION

In accordance with the foregoing objects, the present invention generally comprises a porous pad for insertion substantially into a wound site and a wound drape for air-tight sealing enclosure of the pad at the wound site. A distal end of a tube is connected to the dressing in order to provide negative pressure at the wound site. A fluid sampling port is provided on the tube to allow for sampling of wound fluids being drawn through the tube from the wound site. A source of negative pressure is in communication with a proximal end of the tube. A collection canister is removably connected to the tube for collection of fluid removed from the wound during the application of negative pressure. A first filter is incorporated into an opening of the canister, and a second filter is positioned between the canister and the source of negative pressure. As the source of negative pressure may be an electric pump, supplied by alternating or direct current, a power management device, and its associated power management protocol, is incorporated to maximize battery life when the unit is being supplied by direct current. A clamping mechanism is utilized to secure the system to a stationary object, such as a bed rail, or pole, such as that used to suspend a container of intravenous fluid.

The pad, comprised of a foam having relatively few open cells in contact with the areas upon which cell growth is to be encouraged so as to avoid unwanted adhesions, but having sufficiently numerous open cells so that drainage and negative pressure therapy may continue unimpaired, is placed in fluid communication with a vacuum source for promotion of fluid drainage, as known in the art. The porous pad of the present invention may be comprised of polyvinyl alcohol foam. The fluid communication may be established by connecting a tube to a dressing, such as that described in International Application WO 99/13793, entitled "Surgical Drape and Suction Heads for Wound Treatment," the disclosure of which is incorporated herein.

Upon placement of the pad, an airtight seal is formed over the wound site to prevent vacuum leakage. Such a seal may be provided by placing a drape over the wound, such that the drape adheres to the healthy skin surrounding the wound site, while maintaining an airtight seal over the wound itself.

A conduit or tube is placed in fluid communication with the foam pad, its distal end communicating with a fluid drainage canister which is in fluid communication with a vacuum source. A constant or intermittent negative pressure therapy is conducted as described in the prior art. Alternatively, the negative pressure is varied over time, so as to further stimulate cell growth, which in turn may shorten the healing process. The negative pressure induced on the wound adjusts to meet a varying target pressure, which oscillates between a target maximum and target minimum pressure.

Flow rate of a variable displacement pump, used in accordance with the present invention, is maximized over a pressure range by varying the drive frequency of the pump. The optimum drive frequency is continuously adjusted by a system that periodically or continuously monitors the pressure across the pump to determine the optimum drive frequency for that pressure. Pump performance is thereby improved over variable displacement pumps utilized in the prior art, without increasing pump size or weight. Similarly, pump performance of a typical variable displacement pump can be achieved with a smaller pump, which in turn reduces the size and weight of the overall system in order to improve ease of use and portability for the patient. An alternative negative pressure source, such as a fixed displacement pump, sometimes referred to as a positive displacement pump, may also be utilized.

The power management system is utilized to maximize battery life when the present invention is being supplied with electric power under direct current. The power management system comprises deactivation of a backlight to a display terminal, or touch screen liquid crystal display (LCD) control panel, after a predetermined interval. Battery life is further extended when the power management system prevents electric power from reaching an electric motor until the targeted power setting is actually large enough to activate the motor. In such an instance, the motor is utilized to provide negative pressure by driving an electric pump as known in the art.

The foregoing has outlined some of the more pertinent objects of the present invention. These objects should be construed to be merely illustrative of some of the more prominent features and applications of the invention. Many other beneficial results can be attained by applying the disclosed invention in a different manner or by modifying the invention as will be described. Accordingly, other objects and a fuller understanding of the invention may be had by referring to the following Detailed Description of the Invention, which includes the preferred embodiment.

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which.

DESCRIPTION

Although those of ordinary skill in the art will readily recognize many alternative embodiments, especially in light of the illustrations provided herein, this detailed description is exemplary of the preferred embodiment of the present invention, the scope of which is limited only by the claims that are drawn hereto.

The present invention is a vacuum assisted system for stimulating the healing of tissue.

Figure 1:
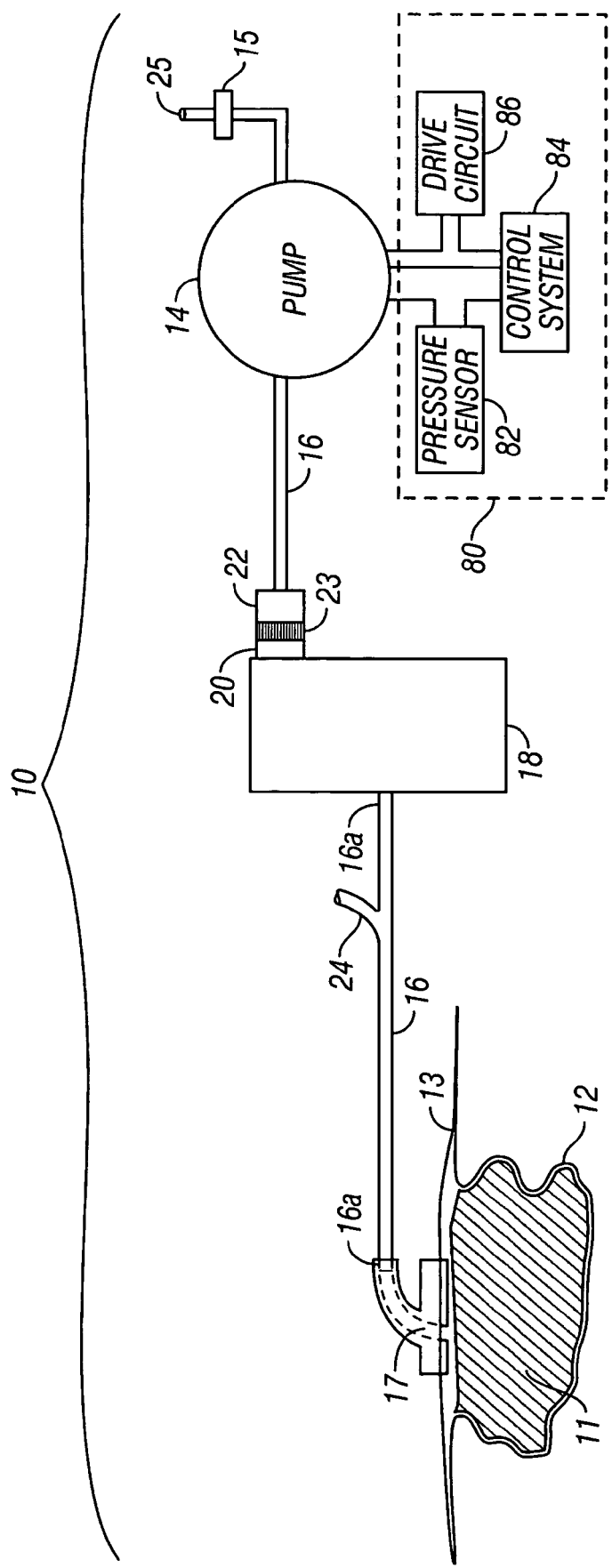
FIG. 1 is a schematic block diagram of a tissue treatment system utilized in accordance with the present invention.

Referring now to FIG. 1 in particular, there is illustrated the primary components of a system that operates in accordance with the present invention. The present invention 10 includes a foam pad 11 for insertion substantially into a wound site 12 and a wound drape 13 for sealing enclosure of the foam pad 11 at the wound site 12. The foam pad 11 may be comprised of a polyvinyl alcohol (PVA) open cell polymer material, or other similar material having a pore size sufficient to facilitate wound healing. A pore density of greater than 38 pores per linear inch is preferable. A pore density of between 40 pores per linear inch and 50 pores per linear inch is more preferable. A pore density of 45 pores per linear inch is most preferable. Such a pore density translates to a pore size of approximately 400 microns.

Addition of an indicating agent, such as crystal violet, methylene blue, or similar agents known in the art causes a color change in the foam 11 when in the presence of a bacterial agent. As such, a user or health care provider can easily and readily ascertain if an infection is present at the wound site 12. It is contemplated that the indicating agent may also be placed in line of the conduit 16, between the wound site 12 and the canister 18. In such a configuration (not shown), the presence of bacterial contaminants in the wound site 12, could be easily and readily ascertained without disturbing the wound bed, as there would be a nearly immediate color change as bacterially infected wound exudates are drawn from the wound site 12 and through the conduit 16 during application of negative pressure.

It is also contemplated that the foam pad 11 may be coated with a bacteriostatic agent. Addition of such an agent, would serve to limit or reduce the bacterial density present at the wound site 12. The agent may be coated or bonded to the foam pad 11 prior to insertion in the wound site, such as during a sterile packaging process. Alternatively, the agent may be injected into the foam pad 11 after insertion in the wound site 12.

After insertion into the wound site 12 and sealing with the wound drape 13, the foam pad 11 is placed in fluid communication with a vacuum source 14 for promotion of fluid drainage and wound healing, as known to those of ordinary skill in the art. The vacuum source 14 may be a portable electrically powered pump, or wall suction as commonly provided in medical care facilities.

According to the preferred embodiment of the present invention, the foam pad 11, wound drape 13, and vacuum source 14 are implemented as known in the prior art, with the exception of those modifications detailed further herein.

The foam pad 11 preferably comprises a highly reticulated, open-cell polyurethane or polyether foam for effective permeability of wound fluids while under suction. The pad 11 is preferably placed in fluid communication, via a plastic or like material conduit 16, with a canister 18 and a vacuum source 14. A first hydrophobic membrane filter 20 is interposed between the canister 18 and the vacuum source 14, in order to prevent wound exudates from contaminating the vacuum source 14. The first filter 20 may also serve as a fill-sensor for canister 18. As fluid contacts the first filter 20, a signal is sent to the vacuum source 14, causing it to shut down. The wound drape 13 preferably comprises an elastomeric material at least peripherally covered with a pressure sensitive adhesive for sealing application over the wound site 12, such that a vacuum seal is maintained over the wound site 12. The conduit 16 may be placed in fluidic communication with the foam 11 by means of an appendage 17 that can be adhered to the drape 13.

According to the preferred method of the present invention, a second hydrophobic filter 22 is interposed between the first filter 20 and the vacuum source 14. The addition of the second filter 22 is advantageous when the first filter 20 is also used as a fill sensor for the canister 18. In such a situation, the first filter 20 may act as a fill sensor, while the second filter 22 further inhibits contamination of wound exudates into the vacuum source 14. This separation of functions into a safety device and a control (or limiting) device, allows for each device to be independently engineered. An odor vapor filter 23, which may be a charcoal filter, may be interposed between the first filter 20 and the second filter 22, in order to counteract the production of malodorous vapors present in the wound exudates. In an alternate embodiment (not shown), the odor vapor filter 23 may be interposed between the second hydrophobic filter 23 and the vacuum source 14. A second odor filter 15 may be interposed between the vacuum source 14 and an external exhaust port 25, in order to further reduce the escape of malodorous vapors from the present system. A further embodiment allows for first 20 and second filters 22 to be incorporated as an integral part of the canister 18 to ensure that the filters 20, 22, at least one of which are likely to become contaminated during normal use, are automatically disposed of in order to reduce the exposure of the system to any contaminants that may be trapped by the filters 20 and 22.

Figure 2A:
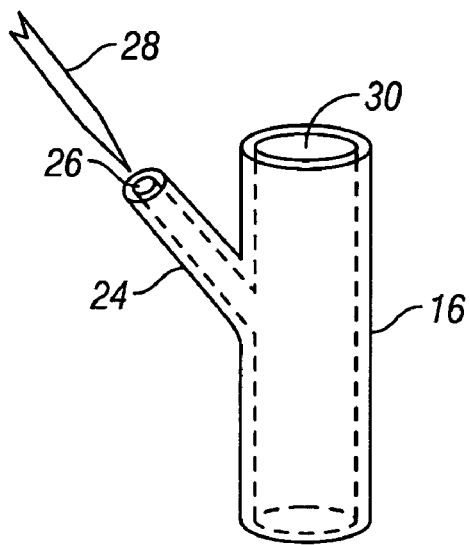
FIG. 2A is a perspective view of a fluid sampling port utilized in accordance with the present invention.
Figure 2B:
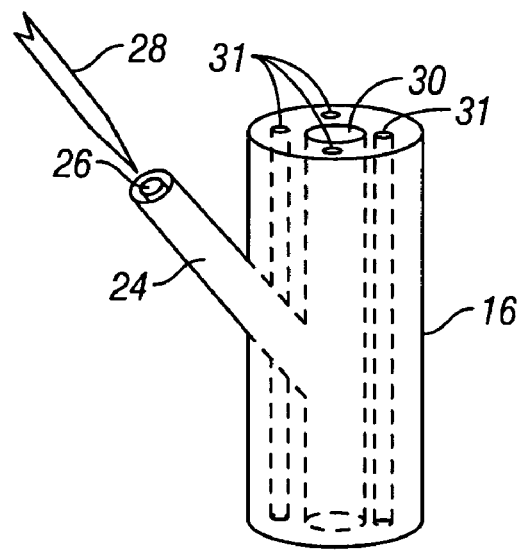
FIG. 2B is a perspective view of an alternative embodiment of a fluid sampling port utilized in accordance with the present invention.

A means for sampling fluids may also be utilized by providing a resealable access port 24 from the conduit 16. The port 24 is positioned between the distal end 16a of the conduit 16 and the proximal end 16b of the conduit 16. The port 24, as further detailed in FIGS. 2a and 2b, is utilized to allow for sampling of fluids being suctioned from the wound site 12. Although the port 24 is shown as an appendage protruding from the conduit 16, it is to be understood that a flush mounted port (not shown) will serve an equivalent purpose. The port 24 includes a resealable membrane 26 that after being punctured, such as by a hypodermic needle, the seal is maintained. Various rubber-like materials known in the art for maintaining a seal after puncture can be utilized.

The process by which wound fluids are sampled, utilizing the present invention, comprises penetrating the membrane 26 with a fluid sampler 28, such as a hypodermic needle or syringe. The sampler 28 is inserted through the membrane 26 and into the port 24 until it is in contact with wound fluids flowing through the inner lumen 30 of the conduit 16. As illustrated in FIG. 2b, and further described in U.S. Pat. No. 6,142,982, issued to Hunt, et al. on May 13, 1998, and whose reference is incorporated herein as though fully set forth, the inner lumen 30 may be surrounded by one or more outer lumens 31. The outer lumens 31 may serve as pressure detection conduits for sensing variations in pressure at the wound site 12. In an alternative embodiment (not shown), the outer lumen or lumens 31 may act as the negative pressure conduit, while the inner lumen 30 may act as the pressure detection conduit. In the present invention, the fluid sampling port 24, communicates only with the inner lumen 30, so as not to interfere with pressure detection that may be conducted by the outer lumens 31. In an alternate embodiment (not shown) in which the outer lumen 31 serves as the negative pressure conduit, the fluid sampling port 24 communicates with the outer lumen 31.

Figure 3A:
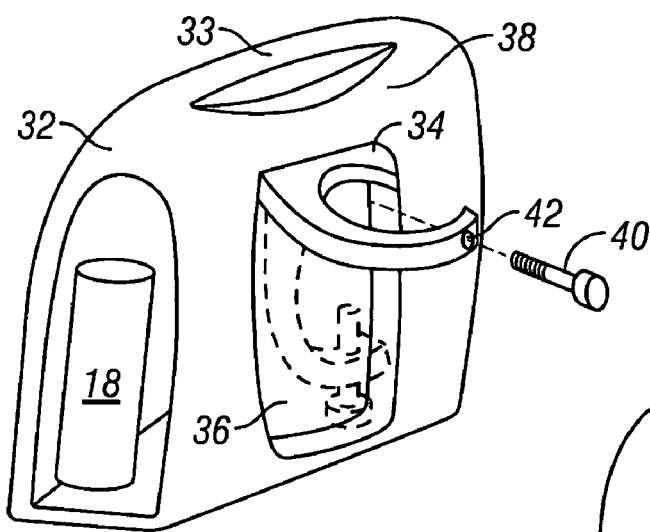
FIG. 3A is a perspective view of the back portion of a pump housing utilized in accordance with the present invention.
Figure 3B:
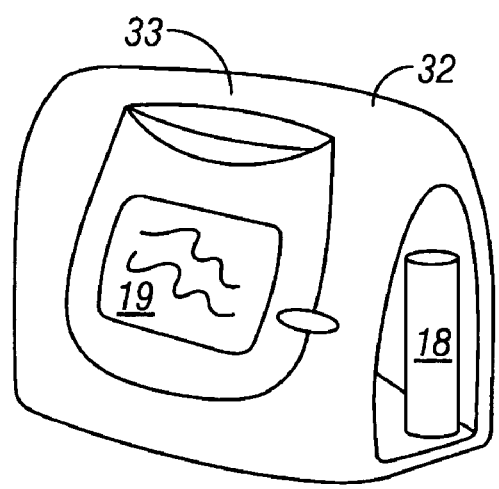
FIG. 3B is a perspective view of the front portion of a pump housing utilized in accordance with the present invention.

The vacuum source 14 may consist of a portable pump housed within a housing 32, as illustrated in FIGS. 3a and 3b. A handle 33 may be formed or attached to the housing 32 to allow a user to easily grasp and move the housing 32.

According to the preferred embodiment of the present invention, a means for securing the housing 32 to a stationary object, such as an intravenous fluid support pole for example, is provided in the form of a clamp 34. The clamp 34, which may be a G-clamp as known in the art, is retractable, such that when not in use is in a stored position within a recess 36 of the housing 32. A hinging mechanism 38 is provided to allow the clamp 34 to extend outward from the housing 32, to up to a 90 degree angle from its stored position. An alternative embodiment (not shown) allows the clamp 34 to be positioned at up to a 180 degree angle from its stored position. The hinging mechanism 38 is such that when the clamp 34 is fully extended, it is locked in position, such that the housing 32 is suspended by the clamp 34. A securing device 40, such as a threaded bolt, penetrates through an aperture 42 of the clamp 34, to allow the clamp 34 to be adjustably secured to various stationary objects of varying thickness.

Alternatively, the securing device 40, may be comprised of a spring actuated bolt or pin, that is capable of automatically adjusting to various objects, such as intravenous fluid support poles, having varying cross-sectional thicknesses.

The present invention also allows for management of a power supply to the vacuum source 14, in order to maximize battery life when the present invention is utilizing a direct current as its power supply. In the preferred embodiment, as illustrated in the flow chart of FIG. 4a, a motor control 44 determines if the actual pressure is less than or equal to a target pressure 46. If the actual pressure is less than the target pressure, a tentative motor drive power required to reach the target pressure is calculated 48. If the tentative motor drive power required to reach the target pressure is greater or equal to the stall power 49, the tentative motor drive power is actually applied to the motor 50. If the actual pressure is greater than the target pressure, the tentative motor drive power is decreased and a determination is made as to whether additional power is needed to overcome the stall power 52. If it is determined that the tentative power is inadequate to overcome the stall power, the tentative power is not supplied to the motor 54. If the tentative power is adequate to overcome the stall power, the tentative power is actually applied to the motor 50. The motor control 44 functions as a closed loop system, such that the actual pressure is continuously measured against the predetermined target pressure. The advantage of such a system is that it prevents power from being supplied to the motor when it is not necessary to maintain the target pressure specified for V.A.C therapy. Accordingly, battery life is extended because power is not needlessly used to power the motor when it is not necessary.

Figure 4B:
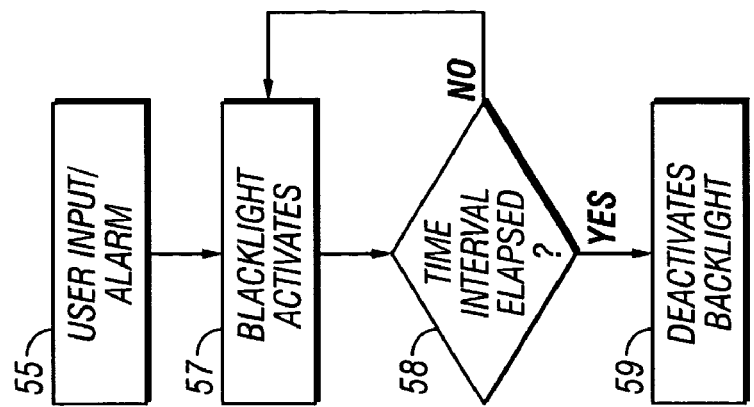
FIGS. 4A and 4B are flow charts representing the preferred steps in the implementation of a power management system utilized in accordance with the present invention.
Figure 4A:
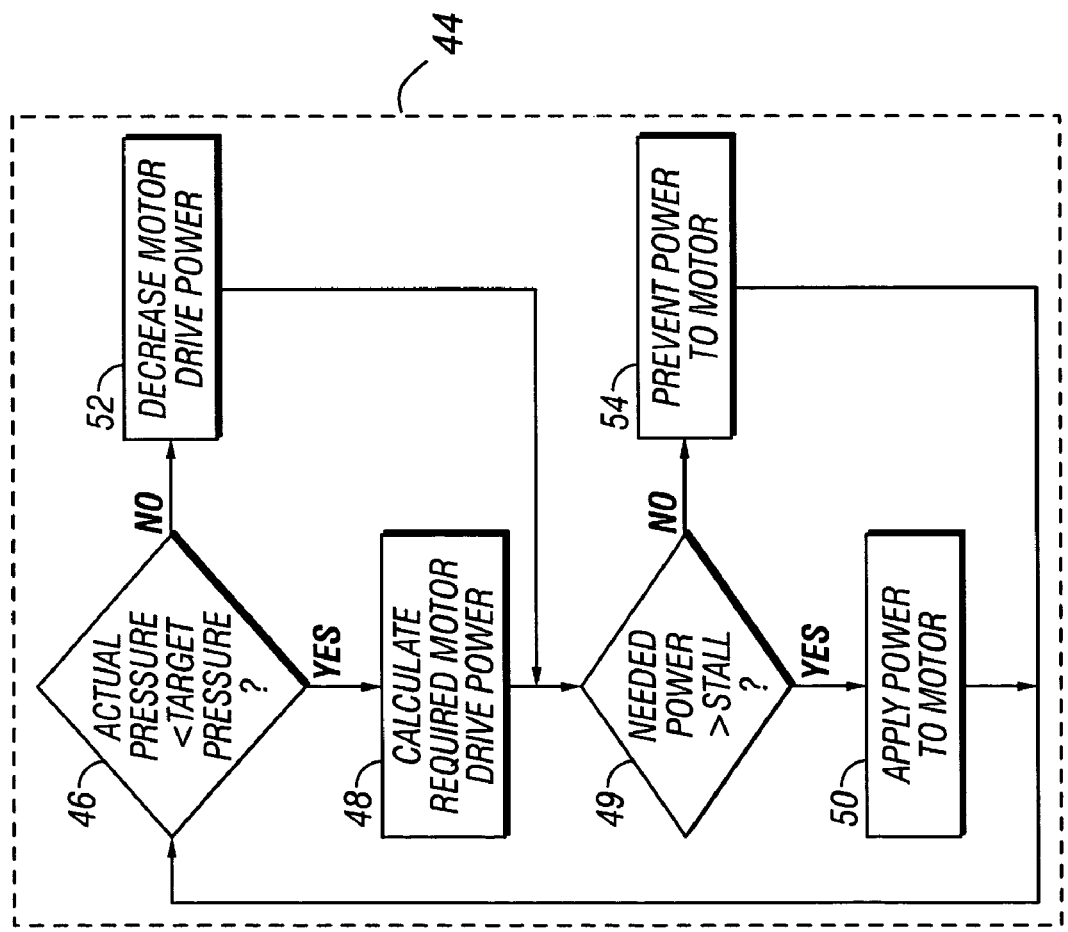

Battery life is further extended, as illustrated in the flow chart shown in FIG. 4b, by providing a means, such as an integrated software program in a computer processor, for automatically disengaging a backlight of the visual display 19 of the present invention 10 (as seen in FIG. 3b). User input of information 55, such as target pressure desired, or duration of therapy, activates 57 a backlight of the visual display 19 shown in FIG. 3b. User input 55 may also be simply touching the visual display 19, which may be a touch activated or a pressure sensitive screen as known in the art. Activation of an alarm 55 may also activate 57 the backlight of the display 19. An alarm may be automatically activated if an air leak is detected at the wound site 12. Such a leak may be indicated by a drop or reduction in pressure being detected at the wound site 12. The backlight remains active until a determination is made as to whether a preset time interval has elapsed 58. If the time interval has not elapsed, the backlight remains active 57. If the time interval has elapsed, the backlight is automatically extinguished 59, until such time as the user inputs additional information, or an alarm is sounded 55.

Referring now back to FIG. 1, battery life is further extended by means of a variable frequency pump drive system 80, when the pump 14, used in accordance with the present invention, is an oscillating pump. The pump drive system 80 consists of a pressure sensor 82, a control system 84, and a variable frequency drive circuit 86. In the preferred embodiment the pressure sensor 82 measures the pressure across the pump, which is relayed to the control system 84. The control system 84 determines the optimum pump drive frequency for the pump 14 given the pressure measured and relayed by the pressure sensor 82. The optimum drive frequency for the pump 14 may be determined by the control system 84 either repeatedly or continuously. The control system 84 adjusts the variable frequency drive circuit 86 to drive the pump at the optimum frequency determined by the control system 84.

The use of the variable frequency pump drive system 80 allows the pressure of the pump 14 to be maximized. In tests on sample oscillating pumps, the maximum pressure achieved was doubled by varying the drive frequency by only 30%. Additionally, the system 80 maximizes flow rate over the extended frequency range. As a result, performance of the pump 14 is significantly improved over existing fixed frequency drive system pumps without increasing the pump size or weight. Consequently, battery life is further extended, thus giving the user greater mobility by not having to be tethered to a stationary power source. Alternatively, a similar performance level to the prior art fixed frequency drive system pumps can be achieved with a smaller pump. As a result, patient mobility is improved by improving the portability of the unit.

Figure 5:
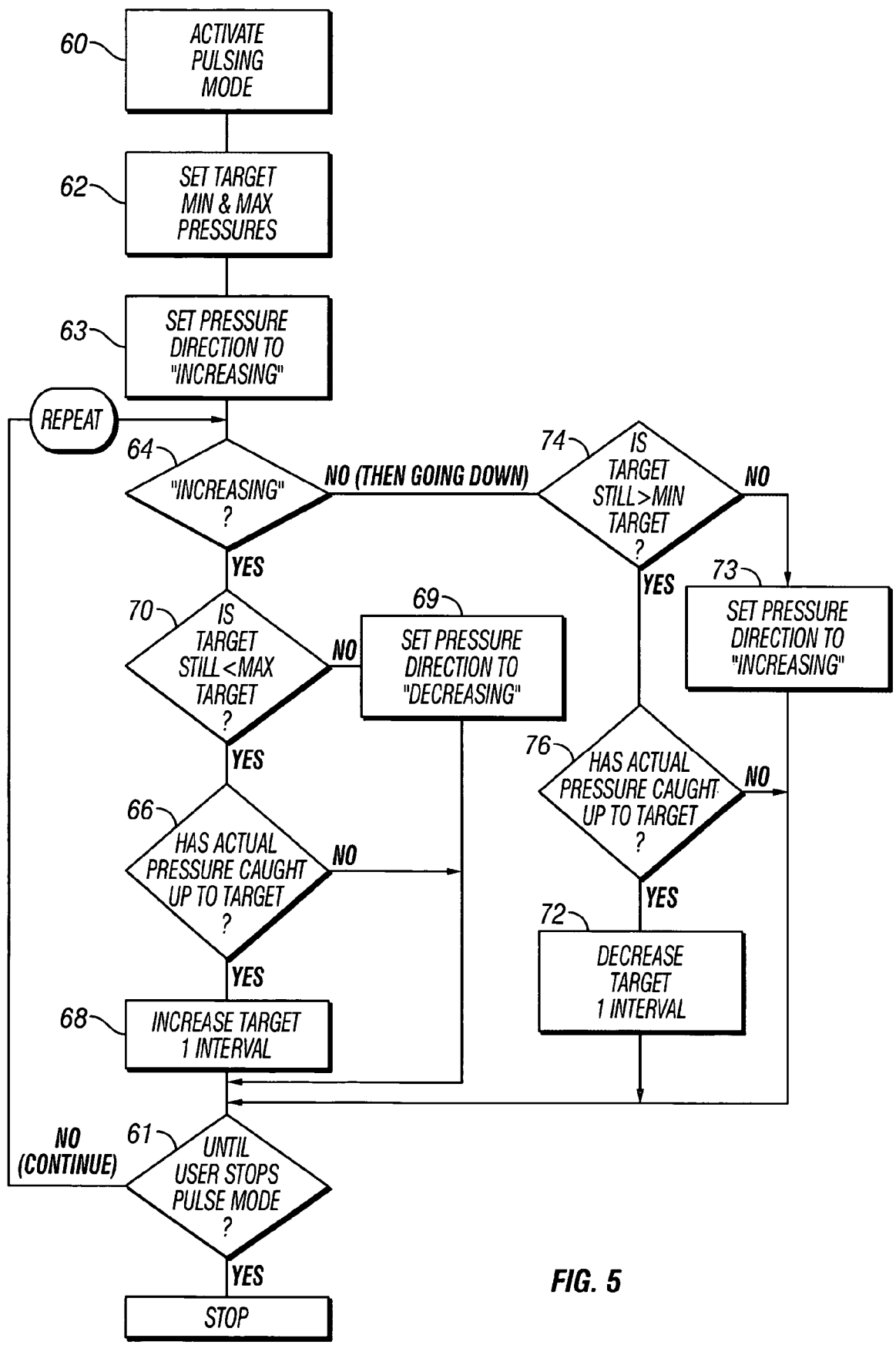
FIG. 5 is a flow chart illustrating the preferred steps in the implementation of pulse therapy utilized in accordance with the present invention.

The preferred embodiment also increases the stimulation of cellular growth by oscillating the pressure over time, as illustrated in the flow chart of FIG. 5. Such an oscillation of pressure is accomplished through a series of algorithms of a software program, utilized in conjunction with a computer processing unit for controlling the function of the vacuum source or pump. The program is initialized when a user, such as a health care provider, activates the pulsing mode of the pump 60. The user then sets a target pressure maximum peak value and a target pressure minimum peak value 62. The software then initializes the pressure direction to "increasing" 63. The software then enters a software control loop. In this control loop, the software first determines if the pressure is increasing 64.

If the actual pressure is increasing in test 64, a determination is then made as to whether a variable target pressure is still less than the maximum target pressure 70. If the variable target pressure is still less than the maximum target pressure the software next determines whether the actual pressure has equaled (risen to) the ascending target pressure 66. If the actual pressure has attained the ascending target pressure, the software increments the variable target pressure by one interval 68. Otherwise, it refrains from doing so until the actual pressure has equaled the ascending target pressure. If the variable target pressure has reached the maximum target pressure in the test of block 70 the software sets the pressure direction to "decreasing" 69 and the variable target pressure begins to move into the downward part of its oscillatory cycle.

The interval may be measured in mmHg or any other common unit of pressure measurement. The magnitude of the interval is preferably in the range of about 1 to 10 mmHg, according to the preference of the user.

If the actual pressure is decreasing in test 64, a determination is then made as to whether the variable target pressure is still greater than the minimum target pressure 74. If the variable target pressure is still greater than the minimum target pressure the software next determines whether the actual pressure has attained (fallen to) the descending target pressure 76. If the actual pressure has equaled the descending target pressure the software decrements the variable target pressure by one interval 72. Otherwise it refrains from doing so until the actual pressure has equaled the descending target pressure. If the variable target pressure has reached the minimum target pressure in the test of block 74, the software sets the pressure direction to "increasing" 73 and the variable target pressure begins to move into the upward part of its oscillatory cycle. This oscillatory process continues until the user de-selects the pulsing mode.

While the invention has been described herein with reference to certain preferred embodiments, these embodiments have been presented by way of example only, and not to limit the scope of the invention. Accordingly, the scope of the invention should be identified only in accordance with the claims that follow.

We claim:

1. A system for stimulating healing of tissue at a wound site comprising:
    a porous pad;
    a pump for applying negative pressure to the wound site through said porous pad that varies over time; and
    a controller regulating the negative pressure applied by the pump by changing the negative pressure in predefined pressure intervals, the controller comparing the negative pressure to a target pressure and incrementing the target pressure toward a maximum target pressure when the negative pressure has risen to or is greater than the target pressure.

2. The system of claim 1, further comprising a drape for covering the porous pad when the porous pad is positioned at the wound site.

3. The system of claim 2, wherein the drape forms an airtight seal around the porous pad.

4. The system of claim 1, further comprising means for deactivating a backlight to a display after a predetermined time interval.

5. The system of claim 1 further comprising a clamp for securing said system to a pole.

6. The system of claim 1, wherein said porous pad is comprised of a polyvinyl alcohol foam.

7. The system of claim 1 further comprising a control system to determine an optimum drive frequency for variably driving the pump in order to maximize pump flow.

8. The system of claim 7, further comprising a pressure sensor for measuring the pressure.

9. The system of claim 8, further comprising a variable frequency drive circuit for driving said pump at said optimum drive frequency.

10. The system of claim 1, wherein said controller is further adapted to compare the target pressure to the maximum target pressure and begin decreasing the negative pressure when the target pressure has reached the maximum target pressure.

11. The system of claim 10, wherein said controller is further adapted to decrement the target pressure toward a minimum target pressure when the negative pressure has fallen to or is less than the target pressure.

12. The system of claim 11, wherein said controller is further adapted to increase the negative pressure when the target pressure has reached the minimum target pressure, whereby the negative pressure oscillates over time between the maximum target pressure and the minimum target pressure.

13. A system for stimulating healing of tissue at a wound site comprising:
   a porous pad;
   a pump for applying negative pressure to the wound site through said porous pad that varies over time; and
   a controller regulating the negative pressure applied by the pump by comparing the negative pressure to a target pressure, said controller being adapted to vary the target pressure between a maximum target pressure and a minimum target pressure by either (a) increasing the target pressure when the negative pressure has risen to or is greater than the target pressure, or (b) decreasing the target pressure when the negative pressure has fallen to or is less than the target pressure.

14. The system of claim 13, wherein said controller is further adapted to compare the target pressure to the maximum target pressure and begin decreasing the negative pressure when the target pressure has reached the maximum target pressure.

15. The system of claim 13, wherein said controller is further adapted to compare the target pressure to the minimum target pressure and begin increasing the negative pressure when the target pressure has reached the minimum target pressure.

16. The system of claim 13, wherein said controller further adapted to decrease the negative pressure when the target pressure has reached the maximum target pressure and increase the negative pressure when the target pressure has reached the minimum target pressure, whereby the negative pressure oscillates over time between the maximum target pressure and the minimum target pressure.

17. A system for stimulating healing of tissue at a wound site comprising:
   a porous pad;
   a pump for applying negative pressure to the wound site through said porous pad that varies over time; and
   a controller regulating the negative pressure applied by the pump and adapted to compare the negative pressure to a target pressure and change the target pressure by (a) incrementing the target pressure toward a maximum target pressure when the negative pressure has risen to or is greater than the target pressure and (b) decrementing the target pressure toward a minimum target pressure when the negative pressure has fallen to or is less than the target pressure.

18. The system of claim 17, wherein said controller is further adapted to (a) decrease the negative pressure when the target pressure has reached the maximum target pressure and (b) increase the negative pressure when the target pressure has reached the minimum target pressure, whereby the negative pressure oscillates over time between the maximum target pressure and the minimum target pressure.

19. A system for stimulating healing of tissue at a wound site comprising:
   a porous pad;
   a pump for applying negative pressure to the wound site through said porous pad that varies over time; and
   a controller regulating the negative pressure applied by the pump by changing the negative pressure in predefined pressure intervals, the controller comparing the negative pressure to a target pressure and decrementing the target pressure toward a minimum target pressure when the negative pressure has fallen to or is less than the target pressure.

20. The system of claim 19, further comprising a drape for covering the porous pad when the porous pad is positioned at the wound site.

21. The system of claim 20, wherein the drape forms an airtight seal around the porous pad.

22. The system of claim 19, further comprising means for deactivating a backlight to a display after a predetermined time interval.

23. The system of claim 19 further comprising a clamp for securing said system to a pole.

24. The system of claim 19, wherein said porous pad is comprised of a polyvinyl alcohol foam.

25. The system of claim 19 further comprising a control system to determine an optimum drive frequency for variably driving the pump in order to maximize pump flow.

26. The system of claim 25, further comprising a pressure sensor for measuring the pressure.

27. The system of claim 26, further comprising a variable frequency drive circuit for driving said pump at said optimum drive frequency.

28. The system of claim 19, wherein said controller is further adapted to compare the target pressure to the minimum target pressure and begin increasing the negative pressure when the target pressure has reached the minimum target pressure.

29. The system of claim 28, wherein said controller is further adapted to increment the target pressure toward a maximum target pressure when the negative pressure has risen to or is greater than the target pressure.

30. The system of claim 29, wherein said controller is further adapted to decrease the negative pressure when the target pressure has reached the maximum target pressure, whereby the negative pressure oscillates over time between the maximum target pressure and the minimum target pressure.

* * * * *